(12) United States Patent
Wang et al.

(10) Patent No.: US 10,934,257 B2
(45) Date of Patent: Mar. 2, 2021

(54) METHOD FOR PREPARING PIMAVANSERIN AND TARTRATE THEREOF BY USING TRIPHOSGENE

(71) Applicant: Livzon New North River Pharmaceutical Co., Ltd., Qingyuan (CN)

(72) Inventors: Biao Wang, Qingyuan (CN); Qiao Jiang, Qingyuan (CN); Bingbing Li, Qingyuan (CN); Murong Peng, Qingyuan (CN); Weijian Xie, Qingyuan (CN)

(73) Assignee: Livzon New North River Pharmaceutical Co., Ltd., Qingyuan (CN)

(*) Notice: Subject to any disclaimer, the term of this patent is extended or adjusted under 35 U.S.C. 154(b) by 0 days.

(21) Appl. No.: 16/764,315

(22) PCT Filed: Jul. 19, 2019

(86) PCT No.: PCT/CN2019/096705
§ 371 (c)(1),
(2) Date: May 14, 2020

(87) PCT Pub. No.: WO2020/020064
PCT Pub. Date: Jan. 30, 2020

(65) Prior Publication Data
US 2020/0369612 A1   Nov. 26, 2020

(30) Foreign Application Priority Data
Jul. 26, 2018 (CN) .......................... 201810832308.0

(51) Int. Cl.
C07D 211/98   (2006.01)

(52) U.S. Cl.
CPC ........ *C07D 211/98* (2013.01); *C07B 2200/07* (2013.01)

(58) Field of Classification Search
CPC .................................................... C07D 211/98
(Continued)

(56) References Cited

U.S. PATENT DOCUMENTS 7,601,740 B2   10/2009   Weiner et al.
7,790,899 B2   9/2010    Tolf et al.

FOREIGN PATENT DOCUMENTS

| CN | 105111135 A | 12/2015 |
| CN | 105418460 A | 3/2016 |

(Continued)

OTHER PUBLICATIONS

Rugang Xie, ed., 1.3.2 Metal hydride and Alcohol-Aluminum Reducing Reagents, Modern Organic Synthetic Chemistry, 1st edition, 1st impression on Jan. 2007, p. 23, East China University of Science and Technology Press.

*Primary Examiner* — Taylor V Oh
(74) *Attorney, Agent, or Firm* — Benjamin Aaron Adler

(57) ABSTRACT

The present disclosure discloses a method for safely preparing pimavanserin and tartrate thereof by using triphosgene. The synthesis route includes:

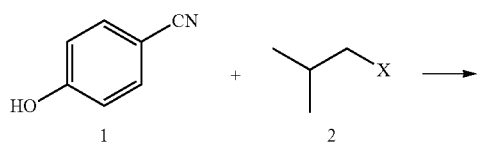

(Continued)

| Detector A 215nm | | | | |
|---|---|---|---|---|
| Peak No. | Compound Name | Retention time | Area | Area% |
| 1 | | 5.930 | 423 | 0.011 |
| 2 | | 7.774 | 879 | 0.022 |
| 3 | | 8.570 | 4020709 | 99.909 |
| 4 | | 12.090 | 2344 | 0.058 |
| Total | | | 4024355 | 100.00 |

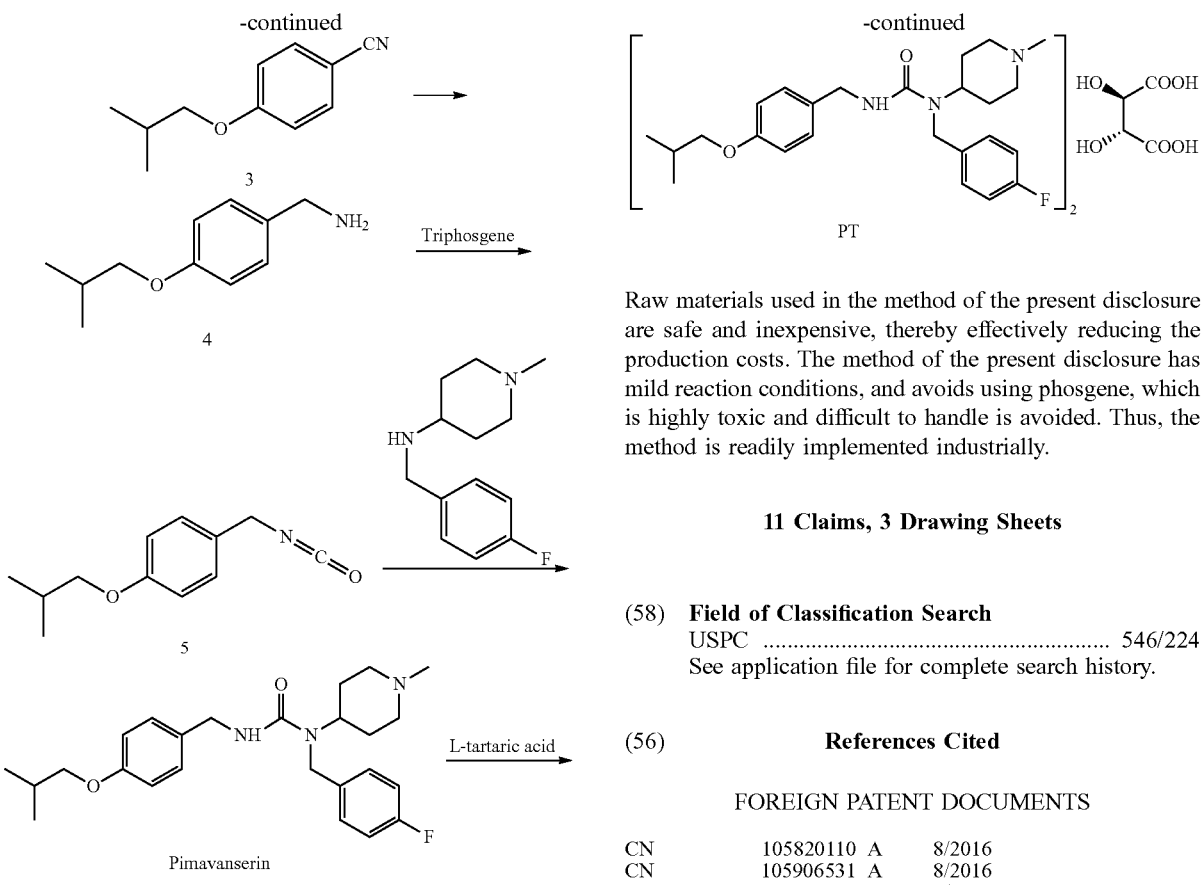

Raw materials used in the method of the present disclosure are safe and inexpensive, thereby effectively reducing the production costs. The method of the present disclosure has mild reaction conditions, and avoids using phosgene, which is highly toxic and difficult to handle is avoided. Thus, the method is readily implemented industrially.

11 Claims, 3 Drawing Sheets

(58) Field of Classification Search
USPC .......................................................... 546/224
See application file for complete search history.

(56) References Cited

FOREIGN PATENT DOCUMENTS

| | | | |
|---|---|---|---|
| CN | 105820110 | A | 8/2016 |
| CN | 105906531 | A | 8/2016 |
| CN | 106588753 | A | 4/2017 |

METHOD FOR PREPARING PIMAVANSERIN AND TARTRATE THEREOF BY USING TRIPHOSGENE

CROSS-REFERENCE TO RELATED APPLICATIONS

This is a national stage application under 35 U.S.C. § 371 of pending international patent application PCT/CN2019/0096705, filed Jul. 19, 2019, which claims the benefit of Chinese Patent Application No. 201810832308.0, filed on Jul. 26, 2018, the entirety of which is hereby incorporated by reference.

TECHNICAL FIELD

The present disclosure relates to the field of synthesis of pharmaceutical molecules, particularly to a process for synthesis of pharmaceutical molecules, and specifically to a method for preparing pimavanserin and pimavanserin tartrate.

BACKGROUND

At present, there are about 7 to 10 million people suffering from Parkinson's disease (PD) in the world, with 2.6 million in China (ranking first in the world). 100,000 new cases are reported each year. More than 50% patients with Parkinson's disease have exhibited Parkinson's disease psychosis (PDP). Main psychotic symptoms comprise hallucinations and delusions, which pose greater challenges for the treatment and nursing of patients with Parkinson's disease. The Parkinson's disease psychosis is one of the main reasons for patients with Parkinson's disease to enter retirement homes. At present, only low-dose clozapine (Clozaril) has been approved for treating Parkinson's disease psychosis. However, clozapine has severe potential safety hazards, and may lead to side effects such as drowsiness and dangerous decrease in the number of white blood cells.

Pimavanserin tartrate (Nuolazid) developed by Acadia Pharmaceuticals, Inc. is a non-dopaminergic neurotransmitter analog for treating Parkinson's disease psychosis. It can selectively block 5-hydroxytryptamine 2A receptors without affecting the functions of dopamine.

Till now, there are few patents relating to the synthesis of pimavanserin.

CN105111135A reports the following synthetic route:

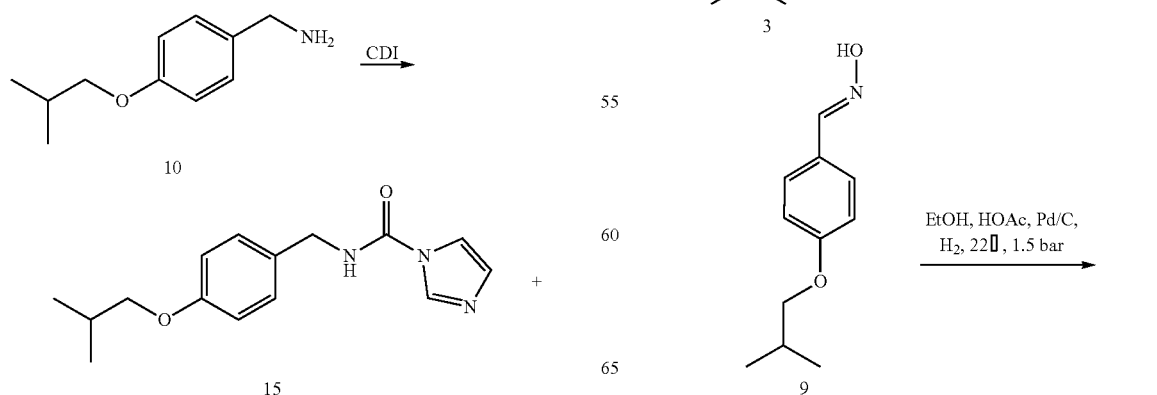

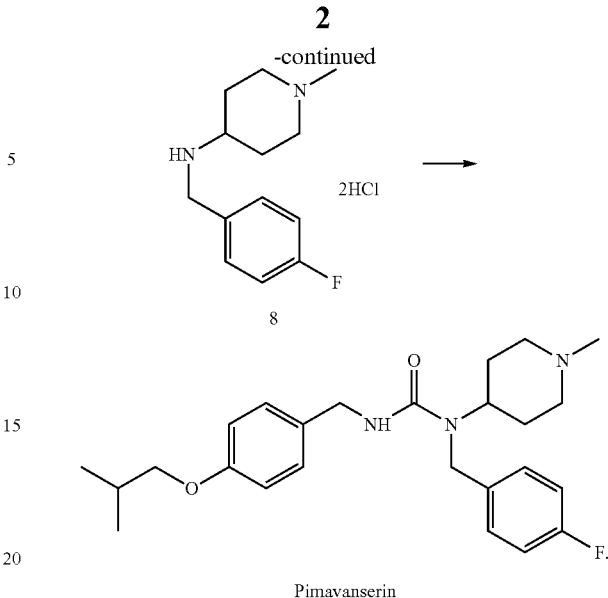

In this synthetic route, carbonyldiimidazole is used as a source for obtaining an active urea intermediate. Although highly toxic and dangerous reagents are avoided, this synthetic route has many steps and the intermediates are not purified. Thus, it is difficult to purify the final product.

CN105418460A discloses a preparation method as the following:

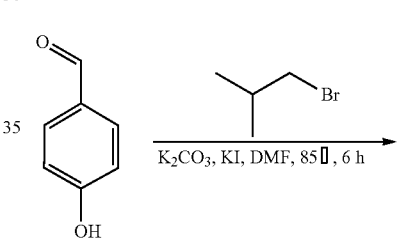

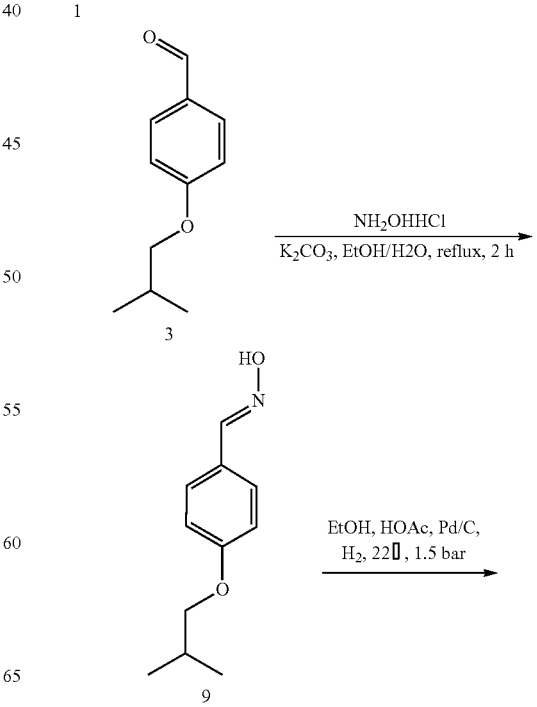

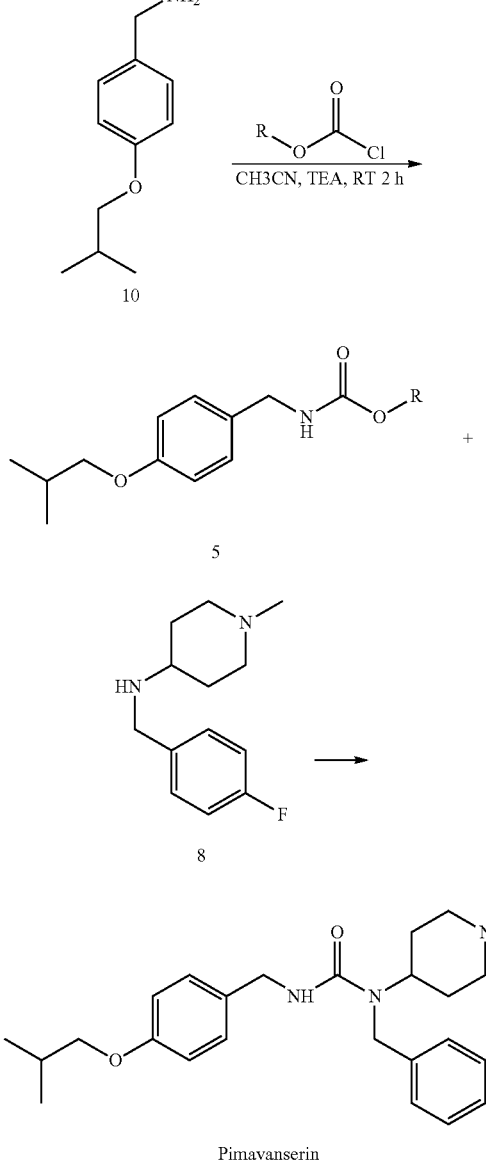

Though this method replaces hypertoxic phosgene with chloroformate, chloroformate is still extremely toxic and would cause severe environmental pollution. Further, this method comprises many reaction steps, and has low yields.

CN201610302251 discloses a preparation method as the following:

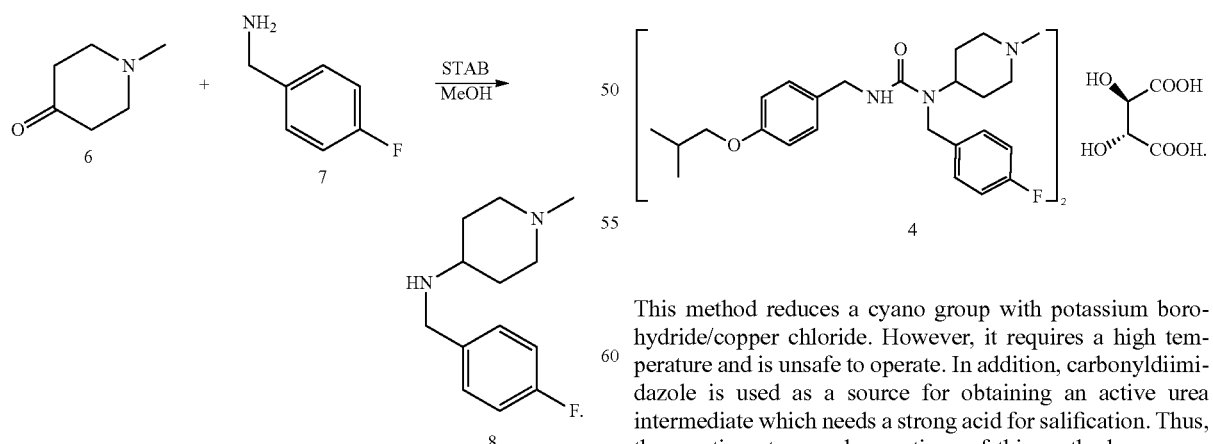

This method reduces a cyano group with potassium borohydride/copper chloride. However, it requires a high temperature and is unsafe to operate. In addition, carbonyldiimidazole is used as a source for obtaining an active urea intermediate which needs a strong acid for salification. Thus, the reaction steps and operations of this method are complex, and are highly corrosive to devices.

U.S. Pat. No. 7,790,899B2 reports a synthetic route as the following:

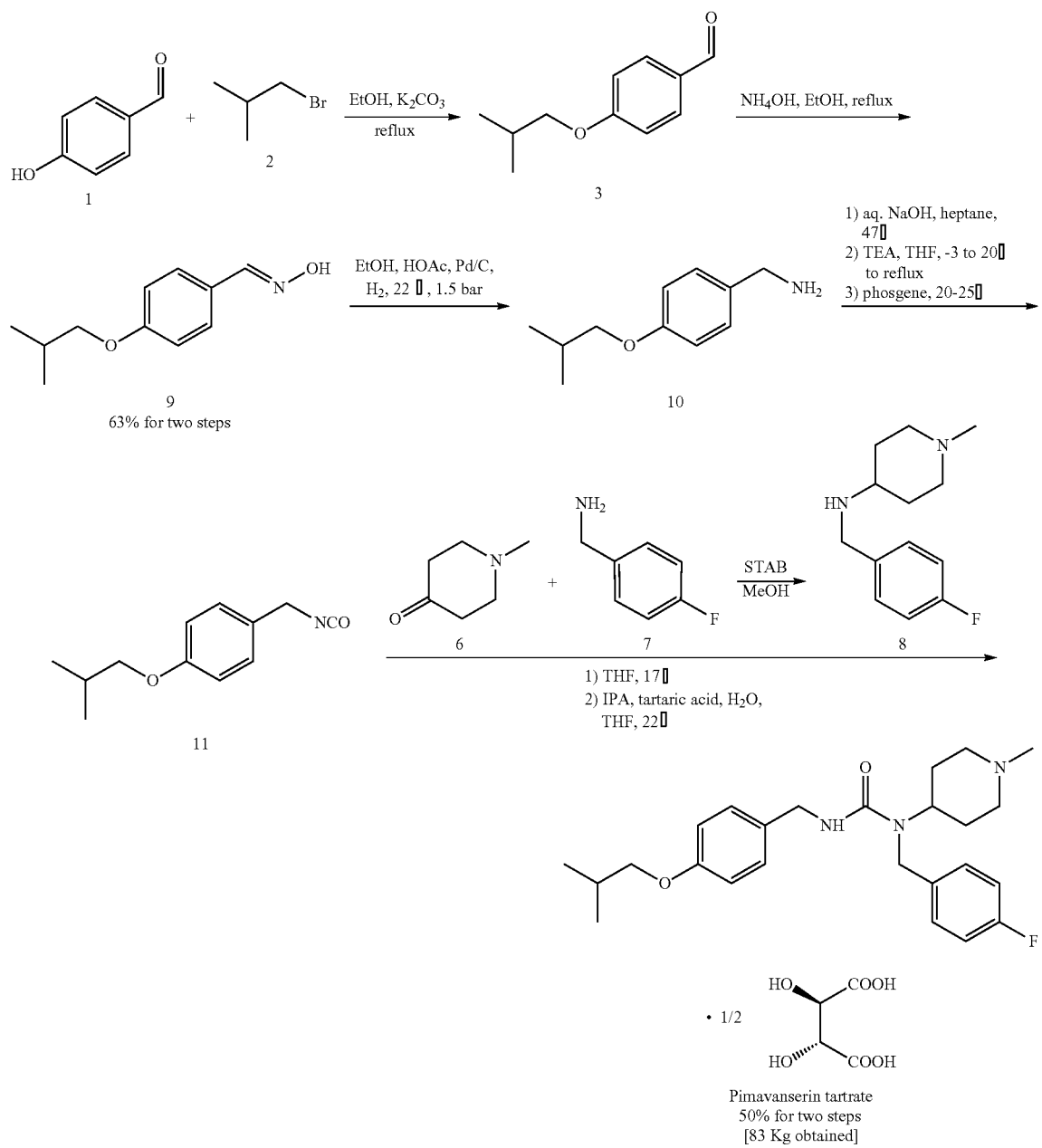

This synthetic route has the following disadvantages. (1) The reaction involves hydrogen and thus needs to be carried out under high pressure, resulting in high safety risks; and the reaction requires an expensive palladium-on-carbon catalyst. (2) The reaction involves toxic phosgene, which has great impact on the health of operators and high safety risks, thereby going against environmental protection and industrial production.

U.S. Pat. No. 7,602,740B2 describes another synthetic route as follows:

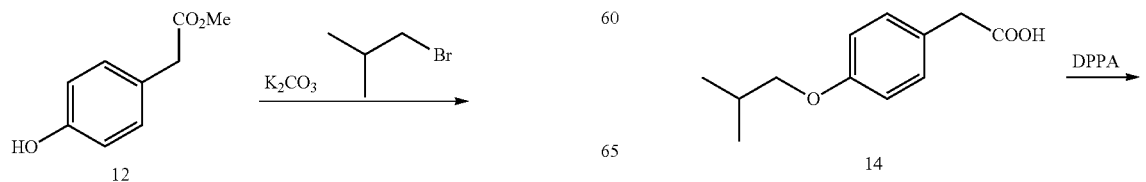

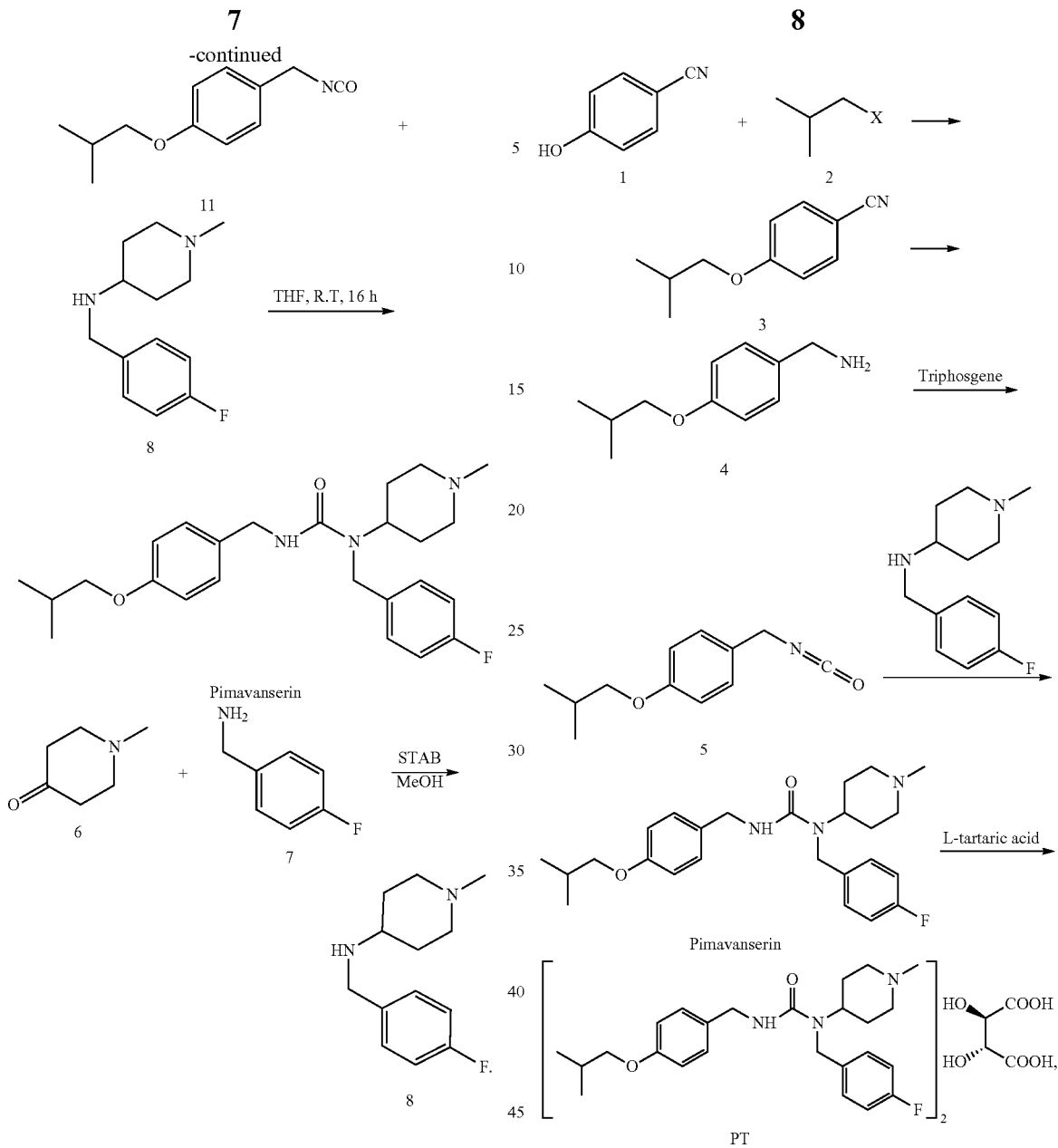

This route uses expensive DPPA. The reaction involves an azide intermediate which has potential safety risks, such as explosion and high toxicity.

It is challenging to develop a method for preparing pimavanserin and a tartrate thereof with mild reaction conditions and fewer reaction steps.

SUMMARY

One object of the present disclosure is to overcome the disadvantages of the prior art, and to provide a method for preparing pimavanserin and pimavanserin tartrate with mild reaction conditions and high yields.

The technical solutions adopted by the present disclosure are as follows.

Provided is a method for safely preparing pimavanserin and tartrate thereof by using triphosgene, which comprise a synthetic route as follows:

wherein X is halogen; and the method comprises the following steps:

1) taking 4-hydroxybenzonitrile and haloisobutane as raw materials, and performing an etherification reaction to obtain 4-isobutoxybenzonitrile;

2) reducing 4-isobutoxybenzonitrile with a reducing agent to obtain 4-isobutoxybenzylamine;

3) performing an acylation reaction with 4-isobutoxybenzylamine and triphosgene, to obtain 4-butoxybenzyl isocyanate; and 4) performing a synthetic reaction with 4-butoxylbenzyl isocyanate and N-(4-fluorobenzyl)-1-methyl-piperidin-4-ylamine, to obtain pimavanserin;

optionally, further salinizing with tartaric acid to obtain pimavanserin tartrate.

According to some embodiments of the present disclosure, a halogenated hydrocarbon may be at least one selected from chloroisobutane, bromoisobutane and iodoisobutane.

According to some embodiments of the present disclosure, the etherification reaction may involve an acid-binding agent which may be any one of potassium carbonate, sodium carbonate, sodium hydroxide, potassium hydroxide, potassium bicarbonate, sodium bicarbonate, diisopropylethylamine, triethylamine, pyridine, ethylenediamine and triethylenediamine, or any combination thereof.

According to some embodiments of the present disclosure, the etherification reaction may involve a solvent which may be any one of acetone, tetrahydrofuran, acetonitrile, 1,4-dioxane, isopropanol, dimethylformamide and dimethylacetamide, or any combination thereof.

According to some embodiments of the present disclosure, the etherification reaction may be performed at a temperature of 10 to 110° C., and preferably 50 to 100° C.

According to some embodiments of the present disclosure, the reducing agent for reducing 4-isobutoxybenzonitrile to 4-isobutoxybenzylamine, may be selected from borane and a borohydride salt.

According to some embodiments of the present disclosure, the borohydride salt may be selected from lithium aluminum hydride, sodium borohydride and potassium borohydride.

According to some embodiments of the present disclosure, the step of reducing 4-isobutoxybenzonitrile to 4-isobutoxybenzylamine may be performed at a temperature of −15 to 70° C., and preferably −15 to 50° C.

According to some embodiments of the present disclosure, the step of reducing 4-isobutoxybenzonitrile to 4-isobutoxybenzylamine may involve a solvent which may be selected from tetrahydrofuran, 1,4-dioxane, methylbenzene, methanol, ethanol and isopropanol.

According to some embodiments of the present disclosure, the step of reducing 4-isobutoxybenzonitrile to 4-isobutoxybenzylamine may involve a catalyst which may be selected from iodine, calcium chloride, nickel chloride, zirconium chloride, copper chloride and indium chloride.

According to some embodiments of the present disclosure, the acylation reaction may involve a solvent which may be an aprotic organic solvent.

According to some embodiments of the present disclosure, in the above step 4), the synthetic reaction for preparing pimavanserin may involve a solvent which may be at least one selected from dichloromethane, trichloromethane, tetrahydrofuran, 1,4-dioxane, acetonitrile, acetone and methylbenzene.

According to some embodiments of the present disclosure, in the above step 4), the the synthetic reaction for preparing pimavanserin may be performed at a temperature of −15 to 100° C., and preferably −15 to 70° C.

According to some embodiments of the present disclosure, (4-fluorobenzyl)-N-(1-methylpiperidin-4-yl)-N'-(4-isobutoxybenzyl)urea and tartaric acid may be dissolved in a solvent A at a molar ratio of 1:(0.5-0.6) and react completely at 40 to 80° C., followed by cooling to crystallize and suction filtering, to give pimavanserin tartrate.

According to some embodiments of the present disclosure, the solvent A may be at least one of anhydrous methanol, anhydrous ethanol, isopropanol, dichloromethane, trichloromethane, methylbenzene, tetrahydrofuran, acetonitrile, or ethyl acetate.

The present disclosure comprises the following beneficial effects.

1) In some embodiments of the present disclosure, the cyano group is reduced by means of a novel synthetic route, using borane and a borohydride salt as the reducing agent and using a chloride salt as a catalyst. Such reaction can achieve excellent selectivity, avoid dangerous reagents such as raney nickel, thereby reducing safety risks during the production of pimavanserin.

2) In some embodiments of the present disclosure, the raw materials used therein are safe and inexpensive, thereby effectively reducing production costs.

3) In some embodiments of the present disclosure, the method of the present disclosure can be readily implemented industrially with mild reaction conditions, and without the use of highly toxic and problematic phosgene.

4) In some embodiments of the present disclosure, it is easy to separate and purify the intermediates and products. The method of the present disclosure may directly proceed with the next step of preparing pimavanserin or pimavanserin tartrate, even without separating the intermediates. Thus, the method of the present disclosure has simple operation, good reproducibility, and higher product quality and yield of pimavanserin as compared to the prior art.

DETAILED DESCRIPTION

Figure 1:
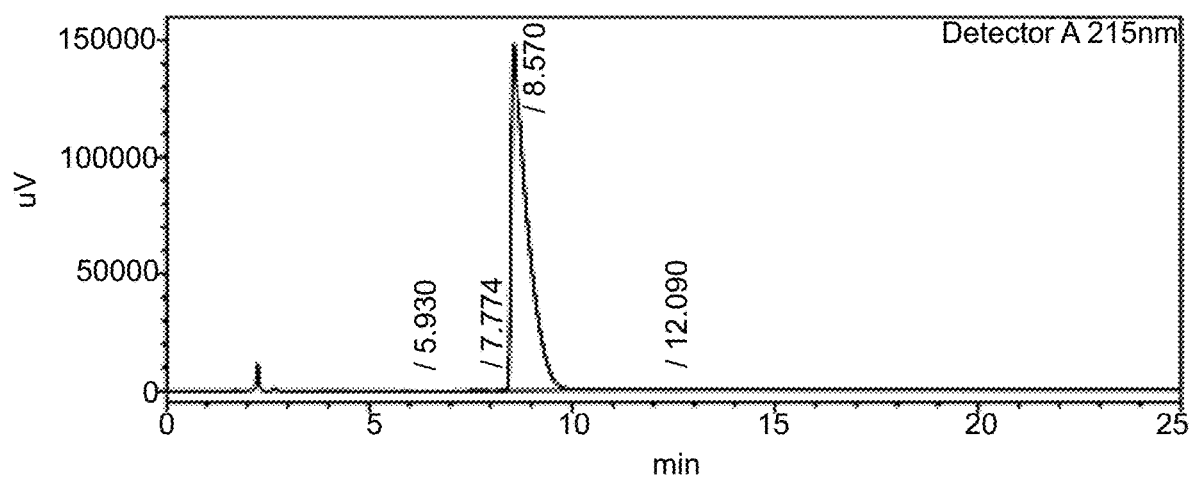
FIG. 1 shows a High-performance liquid chromatography (HPLC) pattern of pimavanserin according to some embodiments of the present disclosure.

A method for safely preparing pimavanserin and tartrate thereof by using triphosgene, comprises a synthetic route as follows:

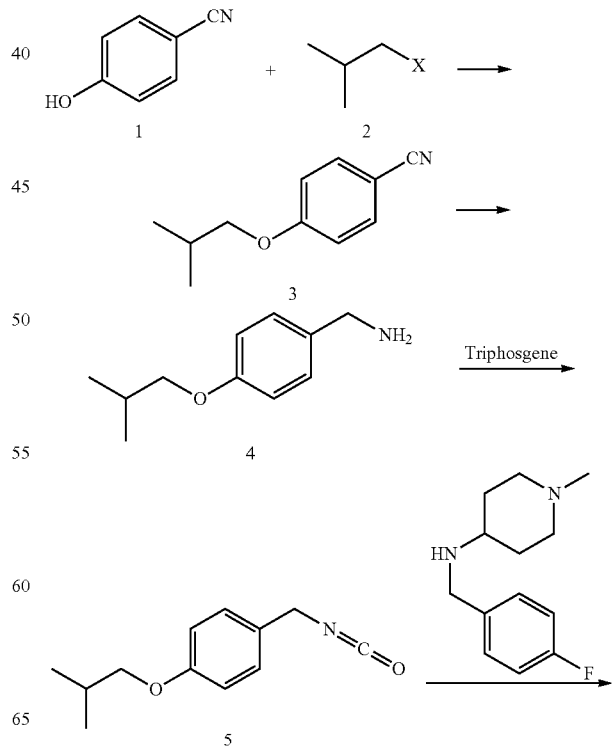

-continued

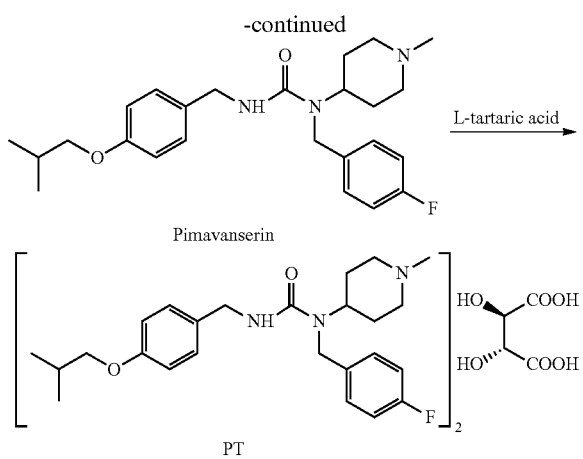

Pimavanserin

PT wherein X is a halogen; and the method comprises the following steps:

1) taking 4-hydroxybenzonitrile and haloisobutane as raw materials, and performing an etherification reaction to obtain 4-isobutoxybenzonitrile;

2) reducing 4-isobutoxybenzonitrile with a reducing agent to obtain 4-isobutoxybenzylamine;

3) performing an acylation reaction with 4-isobutoxybenzylamine and triphosgene, to obtain 4-butoxybenzyl isocyanate; and 4) performing a synthetic reaction with 4-butoxylbenzyl isocyanate and the resulted N-(4-fluorobenzyl)-1-methyl-piperidin-4-ylamine, to obtain pimavanserin;

optionally, further salinizing with tartaric acid to obtain pimavanserin tartrate.

In some embodiments of the present disclosure, a halogenated hydrocarbon may be at least one selected from chloroisobutane, bromoisobutane and iodoisobutane. The optimal halogenated hydrocarbon for different conditions may be determined by monitoring reaction situations.

In some embodiments of the present disclosure, the acid-binding agent, which may be used in the etherification reaction, may be any one of potassium carbonate, sodium carbonate, sodium hydroxide, potassium hydroxide, potassium bicarbonate, sodium bicarbonate, diisopropylethylamine, triethylamine, pyridine, ethylenediamine and triethylenediamine, or any combination thereof. The acid-binding agent can facilitate the initiation of the reaction, and consume the acids generated during the reaction to promote the reaction.

In some embodiments of the present disclosure, the solvent, which may be used in the etherification reaction, may be any one of acetone, tetrahydrofuran, acetonitrile, 1,4-dioxane, isopropanol, dimethylformamide and dimethylacetamide, or any combination thereof. These solvents can promote the reaction better, and reduce the generation of by-products.

If the reaction temperature is low, the reaction would be slow and incomplete; and if the reaction temperature is high, side reactions would be increased, thereby affecting product yield and purity. In some embodiments of the present disclosure, the etherification reaction may be performed at a temperature of 10 to 110° C., and preferably 50 to 100° C. The optimal reaction temperature for each reaction condition can be determined by those skilled in the art by further monitoring the reaction process.

In some embodiments of the present disclosure, the reducing agent for reducing 4-isobutoxybenzonitrile to 4-isobutoxybenzylamine, may be selected from borane and a borohydride salt.

In some embodiments of the present disclosure, the borohydride salt may be selected from lithium aluminum hydride, sodium borohydride and potassium borohydride.

In some embodiments of the present disclosure, a catalyst, which may be used for reducing 4-isobutoxybenzonitrile to 4-isobutoxybenzylamine, may be selected from iodine, calcium chloride, nickel chloride, zirconium chloride, copper chloride and indium chloride.

In some embodiments of the present disclosure, a solvent, which may be used for reducing 4-isobutoxybenzonitrile to 4-isobutoxybenzylamine, may be selected from tetrahydrofuran, 1,4-dioxane, methylbenzene, methanol, ethanol and isopropanol.

The specific borane and borohydride salt may be adjusted based on the used catalyst, solvent and specific reaction conditions, so as to achieve optimal reaction effects.

If the reaction temperature is low, the reaction would be slow and incomplete; and if the reaction temperature is high, side reactions would increase, thereby affecting product yield and purity. Further, if the reaction temperature is too high, the reaction would be violent, and the reactive materials would tend to rush out, which is unfavorable for production operations. In some embodiments of the present disclosure, the step of reducing 4-isobutoxybenzonitrile to 4-isobutoxybenzylamine may be performed at a temperature of −15 to 70° C., and preferably −15 to 50° C. The optimal reaction temperature for each reaction condition can be determined by those skilled in the art by further monitoring the reaction process.

In some embodiments of the present disclosure, a solvent, which may be used for the acylation reaction, may be an aprotic organic solvent, in order to prevent triphosgene from reacting with the solvent during the reaction, and thus prevent generating unnecessary by-products, affecting the yield and the like. The aprotic organic solvent may include, but not limited to, methylbenzene, dichloromethane, trichloromethane, tetrahydrofuran, 2-methyltetrahydrofuran, acetone, and the like. The optimal solvent can be determined comprehensively by monitoring the production of by-products, reaction rates and the like during the reaction.

If the reaction temperature is low, the reaction would be slow and incomplete; and if the reaction temperature is high, side reactions would be increased, thereby affecting product yield and purity. In some embodiments of the present disclosure, the etherification reaction may be performed at a temperature of −15 to 100° C., and preferably −15 to 70° C. The optimal reaction temperature can be determined comprehensively by monitoring the production of by-products, reaction rates and the like during the reaction.

If the reaction temperature is low, the reaction would be slow and incomplete; and if the reaction temperature is high, side reactions would be increased, thereby affecting product yield and purity. In some embodiments of the present disclosure, in step 4), the reaction for preparing pimavanserin may be performed at a temperature of −15 to 100° C., and preferably −15 to 70° C. The optimal reaction temperature can be determined comprehensively by monitoring the production of by-products, reaction rates and the like during the reaction.

In some embodiments of the present disclosure, a solvent, which may be used for preparing pimavanserin in the step 4), may be at least one selected from dichloromethane, trichloromethane, tetrahydrofuran, 1,4-dioxane, acetonitrile, acetone and methylbenzene.

In some embodiments of the present disclosure, (4-fluorobenzyl)-N-(1-methylpiperidin-4-yl)-N'-(4-isobutoxybenzyl)urea and tartaric acid are dissolved in a solvent A at a molar ratio of 1:(0.5-0.6) and react completely at 40 to 80° C., followed by cooling to crystallize and suction filtering, to give pimavanserin tartrate. This can effectively reduce the loss of raw materials, and obtain high-purity pimavanserin tartrate.

In some embodiments of the present disclosure, the above solvent A may be at least one of anhydrous methanol, anhydrous ethanol, isopropanol, dichloromethane, trichloromethane, methylbenzene, tetrahydrofuran, acetonitrile and ethyl acetate.

Any solvent can be used as long as the reaction products can be dissolved well therein, without affecting the normal process of the reactions. In order to improve the production efficiency, it is preferable to use the same solvent in the reactions for preparing pimavanserin and for preparing pimavanserin tartrate.

Hereinafter, the technical solutions of the present disclosure will be further illustrated with reference to the examples.

Some of the raw materials used in the following examples may be prepared by using existing processes, or purchased, or synthesized by using the following processes.

EXAMPLE 1

Preparation of Compound 3 from Compound 1

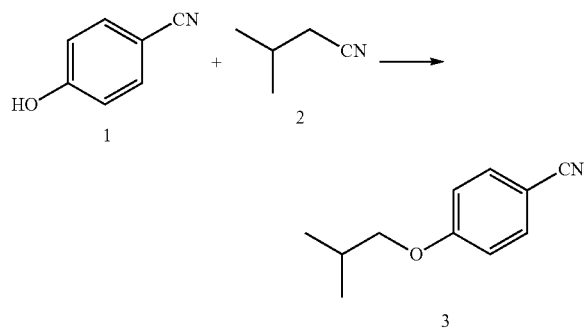

1) Adding p-hydroxybenzaldehyde (14.6 g, 122.8 mmol), anhydrous potassium carbonate (25.4 g, 184.2 mmoL), potassium iodide (1.4 g, 12.3 mmoL), and 75 mL of DMF to a 250 mL three-necked flask, and heating to 85° C.;

2) adding chloroisobutane (34.1 g, 368.4 mmol) slowly to the reaction system, after which the system was kept at 85° C. for 6 h;

3) stopping the reaction, cooling the system to room temperature, filtering, and washing the filter cake with 90 mL of ethyl acetate twice; and 4) pouring the filtrate into 250 mL of water, separating the organic phase, extracting the aqueous phase with 90 mL of ethyl acetate three times, combining the organic phases and washing with 150 mL of saturated brine once, drying over anhydrous sodium sulfate, and filtering. The filtrate was spin-dried to obtain 19.4 g of a compound as light yellow liquid (yield of 90%).

MS (m/z): [M+H]$^+$=176.2; NMR data of the compound 3: $^1$H NMR (400 MHz, CDCl$_3$) (ppm): 7.85 (d, 2H), 7.08 (d, 2H), 3.86 (d, 2H), 1.93-1.85 (m, 1H), 0.96 (d, 6H).

Preparation of Compound 4 from Compound 3

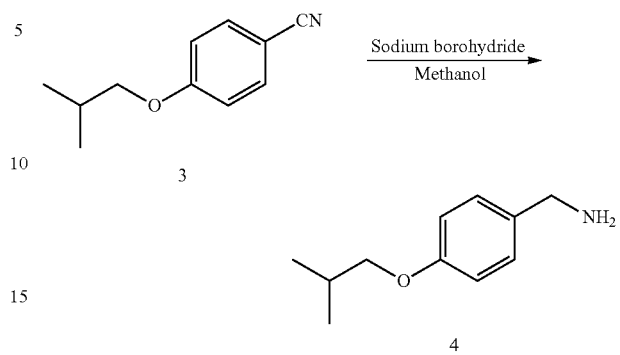

5) Adding 4-isobutoxybenzonitrile (10 g, 57.07 mmol), nickel chloride hexahydrate (13.6 g, 57.07 mmoL), and 150 mL of anhydrous methanol to a 250 mL three-necked flask, displacing with nitrogen three times, cooling to 0 to 10° C. under nitrogen protection, and then adding sodium borohydride (6.5 g, 171.2 mmol) in batches;

6) after the addition of the materials, heating slowly to 20 to 30° C., and maintaining at the temperature for 6 h;

7) filtering the liquid reaction mixture through diatomite, concentrating and evaporating the filtrate to remove most methanol;

8) adding 60 mL of ethyl acetate, slowly adding 10% hydrochloric acid dropwise to adjust pH to pH 1-2, followed by adjusting pH to pH 11-12 with 15% sodium hydroxide solution, stratifying, and extracting the aqueous phase with 60 mL of ethyl acetate, and combining the organic phases; and 9) washing the organic phase with 60 mL of water once and with 60 mL of saturated brine once, drying over anhydrous sodium sulfate, and filtering. The filtrate was spin-dried to obtain 8.6 g of a compound as light yellow liquid (yield of 79%).

MS (m/z): [M+H]$^+$=180.2; NMR data of the compound 4: $^1$H NMR (400 MHz, CDCl$_3$) (ppm): 7.85 (d, 2H), 7.08 (d, 2H), 4.19 (s, 2H), 3.86 (d, 2H), 1.93-1.85 (m, 1H), 0.96 (d, 6H).

Preparation of Compound Pimavanserin from Compound 4

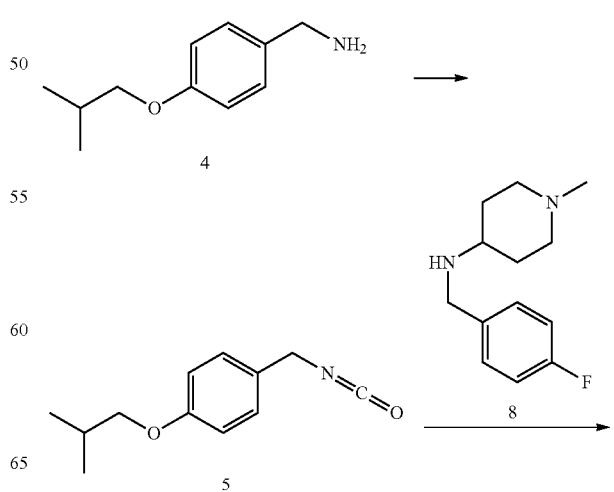

-continued

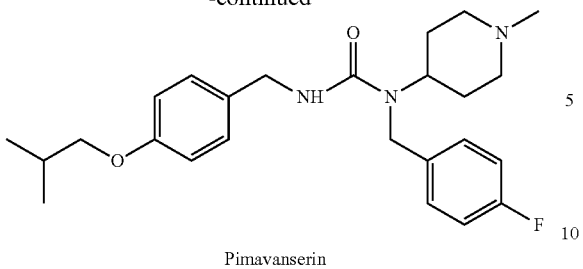

Pimavanserin

10) Adding triphosgene (7.1 g, 24 mmoL) and 86 mL of tetrahydrofuran to a 250 mL three-necked flask, displacing with nitrogen three times, cooling to −10 to 10° C. under nitrogen protection; maintaining the temperature at −10 to 10, and dropwise adding 4-isobutoxybenzylamine/tetrahydrofuran solution (8.6 g, 48.0 mmoL of 4-isobutoxybenzylamine+9.7 g, 96.0 mmoL of triethylamine+43 mL of tetrahydrofuran); after the completion of the dropwise addition, maintaining the temperature at −10 to 10° C. for 4 to 5 hours, maintaining at room temperature for 4 to 5 hours, and refluxing at 65 to 70° C. for 4 to 5 hours; concentrating the solvent was under vacuum until no obvious droplets exist, to obtain crude 4-butoxybenzyl isocyanate; and 11) dissolving the above crude 4-butoxybenzyl isocyanate with 86 mL of tetrahydrofuran in a 250 mL three-necked flask, cooling the system to −10 to 10° C., and stirring for 0.5 h; dropwise adding a solution of Compound 8 (9.6 g, 43.2 mmoL) in tetrahydrofuran (43 mL); after the completion of the dropwise addition, maintaining the system at room temperature for 12 h, and quenching the reaction by slowly adding water dropwise; concentrating at 40 to 50° C. until no obvious fractions exist, extracting and washing with ethyl acetate; drying and concentrating until a large amount of solid precipitated, and dropwise adding n-heptane for crystallization to obtain crude pimavanserin. The crude product was recrystallized with ethanol/water, filtered, and dried to obtain 17.0 g of pimavanserin as white powder.

The yield of the two steps was 83%, and the purity determined by HPLC was 99.9%. [HPLC normalization method: chromatographic column Shimadzu C18 column (250*4.6 mm, 6 μm); mobile phase: 0.1% aqueous solution of phosphoric acid (adjusted to pH=6.5 with triethylamine)-acetonitrile (50:50), detection wavelength of 215 nm; column temperature of 25; flow rate of 1 mL/min]. The HPLC pattern is shown in FIG. 1.

Pimavanserin MS (m/z): [M+H]$^+$=428.6; NMR data: $^1$H NMR (400 MHz, CDCl$_3$) (ppm): 7.35-7.24 (m, 2H), 7.13-7.01 (m, 4H), 6.85 (d, 2H), 5.94 (s, 1H), 4.77 (s, 1H), 4.25 (s, 2H), 3.71 (d, 2H), 3.17-3.05 (m, 2H), 2.41-2.34 (m, 4H), 2.7 (s, 3H), 1.86-1.54 (m, 4H), 0.95 (d, 6H).

EXAMPLE 2

Preparation of Compound 3 from Compound 1

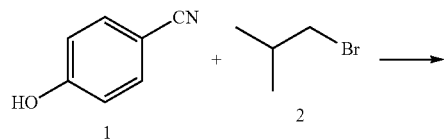

-continued

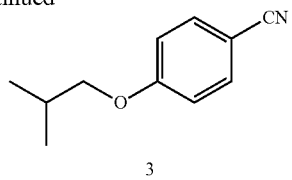

3

1) Adding p-hydroxybenzaldehyde (14.6 g, 122.8 mmol), anhydrous potassium carbonate (25.4 g, 184.2 mmoL), potassium iodide (1.4 g, 12.3 mmoL), and 75 mL of DMF to a 250 mL three-necked flask, and heating to 90° C.;

2) slowly adding bromoisobutane (50.5 g, 368.4 mmol) the reaction system, and then maintaining the system at 90° C. for 5 h;

3) stopping the reaction, cooling the system to room temperature, filtering, and washing the filter cake with 90 mL of ethyl acetate twice; and 4) pouring the filtrate into 250 mL of water, separating the organic phase, and extracting the aqueous phase with 90 mL of ethyl acetate three times respectively; combining the organic phases, washing with 150 mL of saturated brine once, drying over anhydrous sodium sulfate, and filtering. The filtrate was spin-dried to obtain 19.8 g of a compound as light yellow liquid, yield 92%.

Preparation of Compound 4 from Compound 3

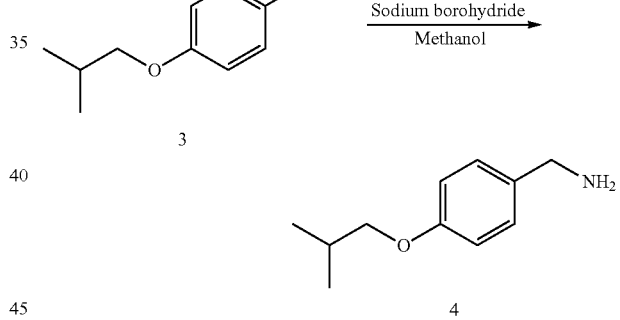

5) Adding 4-isobutoxybenzonitrile (10 g, 57.07 mmol), indium chloride (12.6 g, 57.07 mmoL), and 150 mL of anhydrous methanol to a 250 mL three-necked flask; displacing with nitrogen three times, cooling to 0 to 10° C. under nitrogen protection; adding sodium borohydride (6.5 g, 171.2 mmol) in batches;

6) after the completion of the addition of the materials, slowly heating to 30 to 35° C., and maintaining at the temperature for 6 h;

7) filtering the liquid reaction mixture through diatomite, concentrating and evaporating the filtrate to remove most methanol;

8) adding 60 mL of ethyl acetate, adjusting pH to pH 1 to 2 by slowly adding 10% hydrochloric acid dropwise, and then adjusting pH to pH 11 to 12 with 15% sodium hydroxide solution; stratifying, extracting the aqueous phase with 60 mL of ethyl acetate, and combining the organic phases; and 9) washing the organic phase with 60 mL of water once and then with 60 mL of saturated brine once, drying over anhydrous sodium sulfate, and filtering. The filtrate was spin-dried to obtain 7.3 g of a compound as light yellow liquid (yield of 72%).

Preparation of Compound Pimavanserin from Compound 4

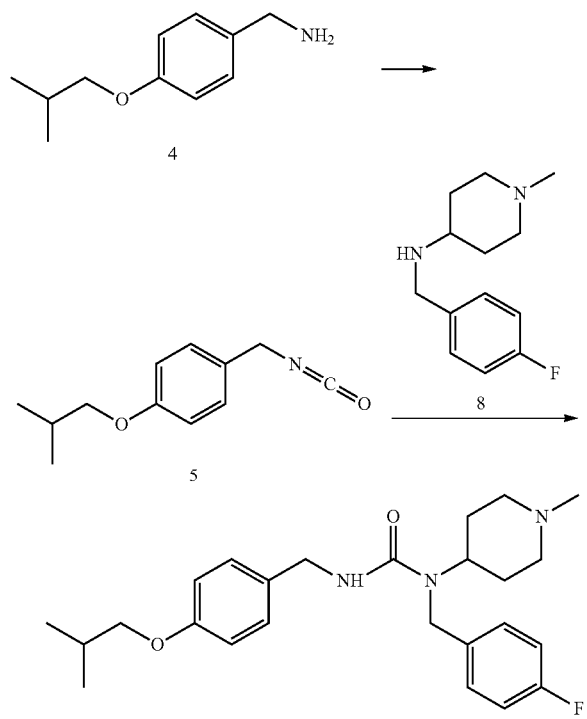

10) Adding triphosgene (7.1 g, 24 mmoL) and 86 mL of methylbenzene to a 250 mL three-necked flask, displacing with nitrogen three times, cooling to −10 to 10° C. under nitrogen protection; maintaining the temperature at −10 to 10° C., and dropwise adding 4-isobutoxybenzylamine/methylbenzene solution (8.6 g 48.0 mmoL of 4-isobutoxybenzylamine+9.7 g, 96.0 mmoL of triethylamine+43 mL of methylbenzene); after the dropwise addition, maintaining the system at −10 to 10° C. for 4 to 5 hours, at room temperature for 4 to 5 hours, and then at 60 to 70° C. for 1 to 2 hour(s); concentrating the solvent under vacuum until no obvious droplets exist, to obtain crude 4-butoxybenzyl isocyanate; and 11) dissolving the above crude 4-butoxybenzyl isocyanate with 86 mL of methylbenzene in a 250 mL three-necked flask; cooling the system to −10 to 10° C., and stirring for 0.5 h; dropwise adding a solution of Compound 8 (9.6 g, 43.2 mmoL) in methylbenzene (43 mL); after the dropwise addition, maintaining at room temperature for 12 h, quenching the reaction by slowly adding water dropwise; leaving to stand for stratification, and extracting with methylbenzene twice; washing the organic phase with water, drying, and concentrating until a large amount of solid precipitated; dropwise adding n-heptane for crystallization, to obtain crude pimavanserin. The crude product was recrystallized with ethanol/water, filtered, and dried to obtain 16.6 g of pimavanserin as white powder. The yield of the two steps was 81%, and the purity determined by HPLC was 99.8%.

EXAMPLE 3

Preparation of Compound 3 from Compound 1

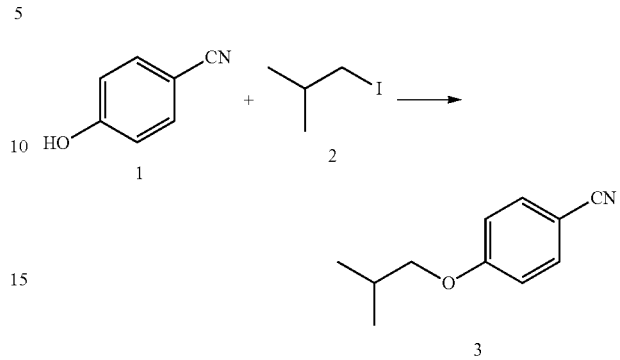

1) Adding p-hydroxybenzaldehyde (14.6 g, 122.8 mmol), anhydrous potassium carbonate (25.4 g, 184.2 mmoL), potassium iodide (1.4 g, 12.3 mmoL), and 75 mL of DMF to a 250 mL three-necked flask, and heating to 100° C.;

2) slowly adding iodoisobutane (67.8 g, 368.4 mmol) to the reaction system, and then maintaining the system at 100 for 5 h;

3) stopping the reaction, cooling the system to room temperature, filtering, and washing the filter cake with 90 mL of ethyl acetate twice; and 4) pouring the filtrate into 250 mL of water, separating the organic phase, and extracting the aqueous phase with 90 mL of ethyl acetate three times; combining the organic phases, washing with 150 mL of saturated brine once, drying over anhydrous sodium sulfate, and filtering. The filtrate was spin-dried to obtain 19.6 g of a compound as light yellow liquid (yield of 91%).

Preparation of Compound 4 from Compound 3

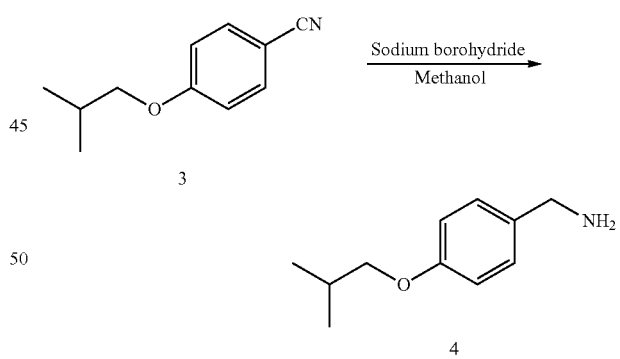

5) Adding 4-isobutoxybenzonitrile (10 g, 57.07 mmoL), copper chloride (9.7 g, 57.07 mmoL), and 150 mL of anhydrous methanol to a 250 mL three-necked flask, displacing with nitrogen, cooling to 0 to 10° C. under nitrogen protection; adding sodium borohydride (6.5 g, 171.2 mmoL) in batches;

6) after the completion of the addition of the materials, slowly heating the system to 40 to 50° C., and maintaining at the temperature for 6 h;

7) filtering the liquid reaction mixture through diatomite, concentrating and evaporating the filtrate to remove most methanol;

8) adding 60 mL of ethyl acetate, adjusting pH to pH 1-2 by slowly adding 10% hydrochloric acid dropwise, and then adjusting pH to 11-12 with 15% sodium hydroxide solution. stratifying, extracting the aqueous phase with 60 mL of ethyl acetate, and combining the organic phases; and 9) washing the organic phase with 60 mL of water once and with 60 mL of saturated brine once, drying over anhydrous sodium sulfate, followed by filtering. The filtrate was spin-dried to obtain 7.0 g of a compound as light yellow liquid (yield of 69%).

Preparation of Compound Pimavanserin from Compound 4

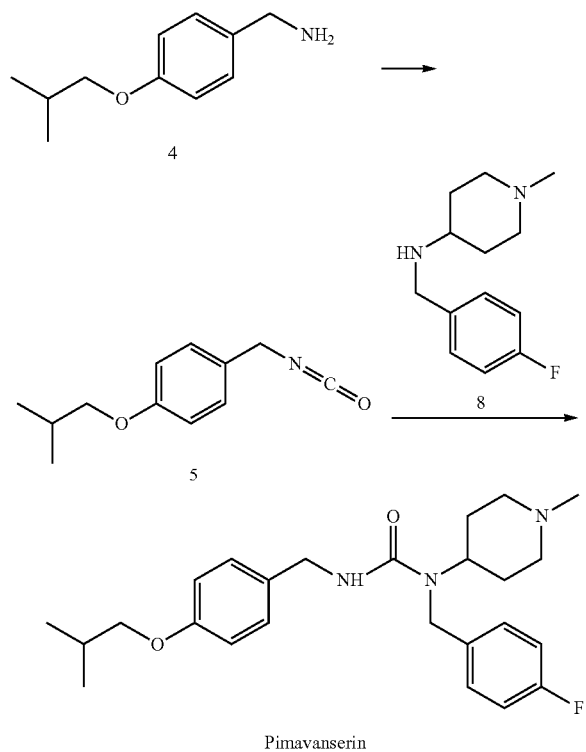

10) Adding triphosgene (7.1 g, 24 mmoL) and 86 mL of dichloromethane to a 250 mL three-necked flask, displacing with nitrogen three times, cooling to −10 to 10° C. under nitrogen protection; maintaining the temperature at −10 to 10° C., and dropwise adding 4-isobutoxybenzylamine/dichloromethane solution (8.6 g 48.0 mmoL of 4-isobutoxybenzylamine+9.7 g, 96.0 mmoL of triethylamine+43 mL of dichloromethane); then, maintaining the system at −10 to 10° C. for 4 to 5 hours and at room temperature for 4 to 5 hours, and refluxing at 35 to 40° C. for 4 to 5 hours; concentrating the solvent under vacuum until no obvious droplets exist, to obtain crude 4-butoxybenzyl isocyanate;

11) dissolving the above crude 4-butoxybenzyl isocyanate with 86 mL of methylbenzene in a 250 mL three-necked flask; cooling the system to −10 to 10° C., and stirring for 0.5 h; dropwise adding a solution of Compound 8 (9.6 g, 43.2 mmoL) in dichloromethane (43 mL); then, maintaining the system at room temperature for 12 h, followed by slowly adding water dropwise to quench the reaction, and leaving to stand for stratification; extracting with dichloromethane twice, washing the organic phase with water, drying, and then concentrating until a large amount of solid precipitated; and then dropwise adding n-heptane for crystallization, to obtain crude pimavanserin. The crude product was recrystallized with ethanol/water, filtered, and dried to obtain 16.0 g of pimavanserin as white powder. The yield of the two steps was 78%, with 99.8% purity determined by HPLC.

The results of the Examples show that the method of the present disclosure can easily obtain high-purity pimavanserin, and the yields are significantly higher than those of the prior art.

The synthetic routes described in literatures and patents were repeated to obtain the data relating to the yield and purity thereof, and compared with that of the present disclosure:

Comparative Example 1: Preparation of pimavanserin tartrate by using the method disclosed in U.S. Pat. No. 7,790,899B2

Comparative Example 2: Preparation of pimavanserin by using the method disclosed in CN105418460A Table 1 shows the comparison results for the different preparation methods of pimavanserin.

TABLE 1

Comparison Results for Different Preparation Methods of Pimavanserin

| No. | Number of reaction steps | Key reaction | Purity | Total yield |
|---|---|---|---|---|
| Comparative Example 1 | 7 | Reduction of C═N double bond Reagents: raney nickel, H$_2$; CH$_3$OH | 98.4% | 30.4% |
| Comparative Example 2 | 5 | Reduction of C═N double bond Reagent: Pd/C, H$_2$; CH$_3$OH | 99.0% | 20.9% |
| Example 1 | 4 | Reduction of Cyano group Reagents: NaBH$_4$/nickel chloride hexahydrate; CH$_3$OH | 99.9% | 59.0% |
| Example 2 | 4 | Reduction of Cyano group Reagents: NaBH$_4$/nickel chloride; CH$_3$OH | 99.8% | 53.6% |
| Example 3 | 4 | Reduction of Cyano group Reagents: NaBH$_4$/copper chloride; CH$_3$OH | 99.8% | 49.0% |

As can be seen from the data in the above table:

The method of the present disclosure significantly reduces the amount of impurities in the product by changing the synthetic process. As compared with Comparative Examples 1 and 2, the amount of impurities is significant reduced from 1.6% and 1.0% to 0.1-0.2%, respectively. The method of the present disclosure is more controllable in the product quality, and greatly reduces the purification difficulty for the product.

As compared with Comparative Example 1, Examples 1, 2, and 3 are different in that fewer reaction steps are involved; the use of raney nickel and phosgene is avoided; and, the intermediates are not subject to salification to being free forms before involving in the reactions. Thus, the method of the present disclosure has simplified steps, lower material costs, safer preparation of the product, and significantly improved yield.

As compared with Comparative Example 2, Examples 1, 2, and 3 are different in that a NaBH$_4$/chloride salt system is used for reduction; the intermediates are not subject to salification to being free forms before involving in the reactions; and, pimavanserin does not need to be purified by column chromatography. Thus, the method of the present disclosure has lower material costs, simplified operations, and improved product yield.

By comparing Examples 1, 2, and 3, it is found that the NaBH$_4$/nickel chloride hexahydrate reduction system has the best reduction effect, and significant increased the yield. It is presumed that sodium borohydride reacts with nickel chloride to generate a boron-nickel compound, which has high catalytic activity, and hydrogen. Thus, the cyano group can be catalytically reduced to an amino group efficiently.

In conclusion, it can simplify the synthetic process of pimavanserin tartrate by carrying out the reactions using the process parameters of the present disclosure. In addition, the method of the present disclosure has mild reaction conditions and simple operation steps, thereby significantly improving the product quality and yield, and reducing the synthesis cost of pimavanserin tartrate.

Preparation of Pimavanserin Tartrate from Pimavanserin

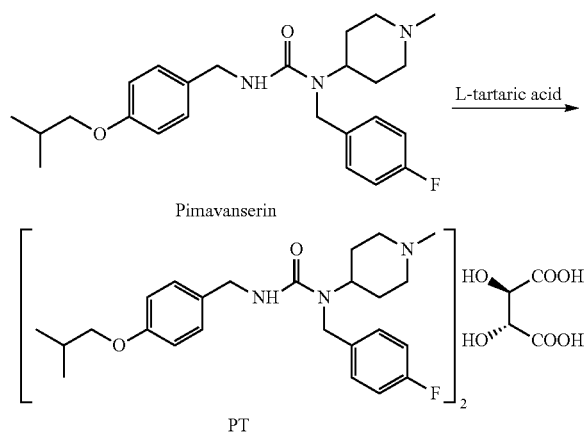

Figure 2:
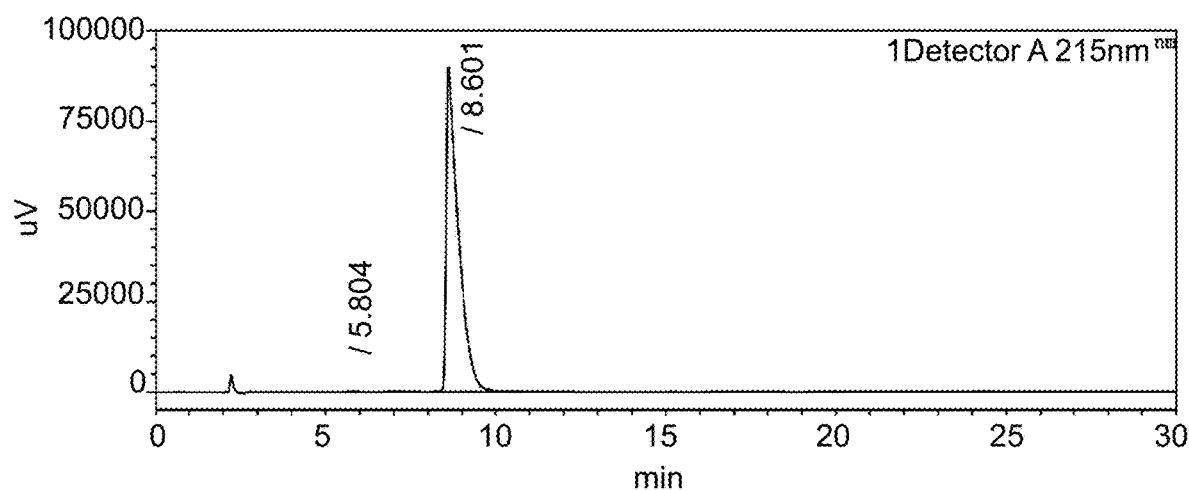
FIG. 2 shows a HPLC pattern of pimavanserin tartrate according to some embodiments of the present disclosure.
Figure 3:
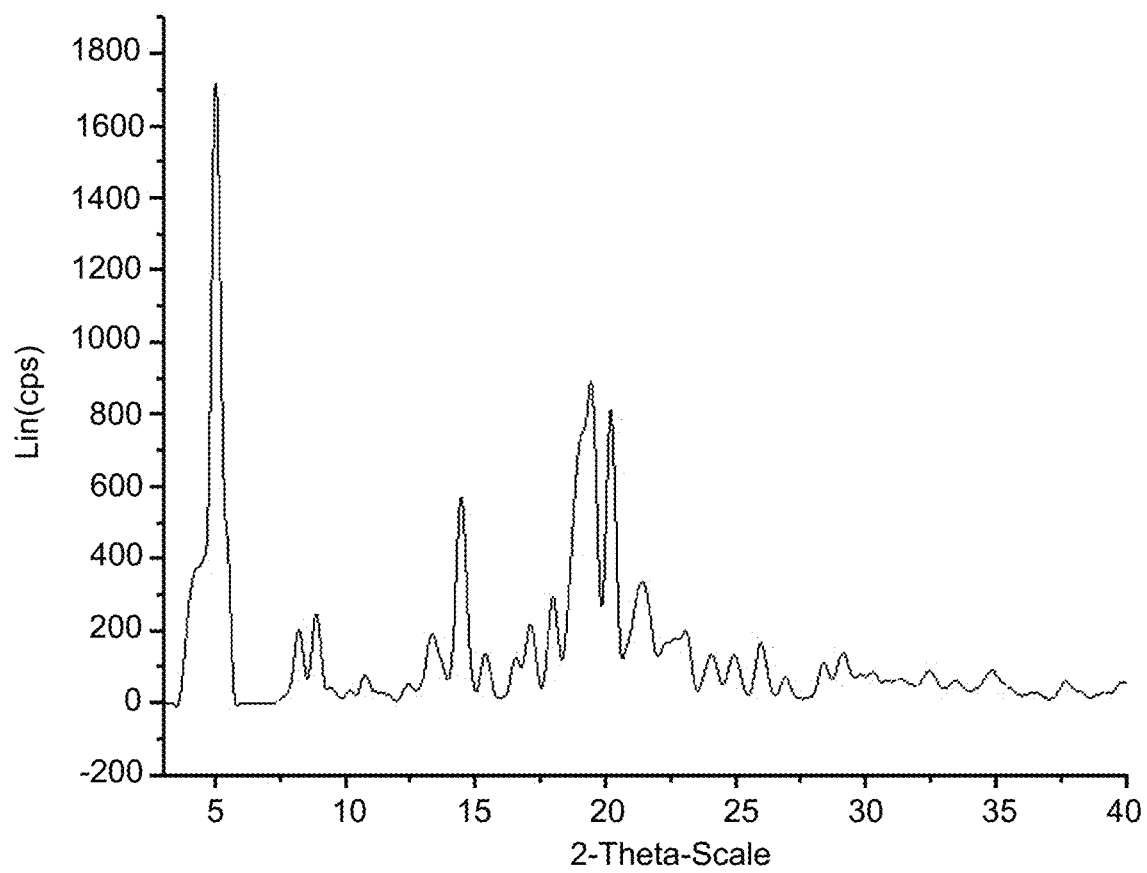
FIG. 3 shows an X-ray diffraction pattern (XRD) pattern of HPLC crystal form I of pimavanserin tartrate according to some embodiments of the present disclosure.

90 mL of isopropanol, 6 g of pimavanserin, 1.08 g of L-tartaric acid, and 6 mL of dichloromethane were added to a 250 mL three-necked flask, displaced with nitrogen, heated to 70±5° C. under nitrogen protection, then maintained at the temperature for 5 h, followed by slowly cooling to 0 to 5° C., maintaining at the temperature for 2 h, and then filtering. The filter cake was rinsed with 9 mL of pre-cooled isopropanol, and the wet product was dried under vacuum at 60° C. to obtain 6.5 g of pimavanserin tartrate as white powder, with yield of 93%, purity of 99.9% (HPLC pattern is shown in FIG. 2) and isopropanol of 2.0% (having isopropanol solvate of pimavanserin tartrate). Based on XRD (FIG. 3), it is determined to be crystal form I. DSC shows that the melting point is about 128° C., and the melting enthalpy is about 75.02 J/g.

Table 2 shows the X-ray powder diffraction characteristic peak data of the resulted solid.

TABLE 2

| X-Ray Powder Diffraction Characteristic Peak Data of the Resulted Pimavanserin Tartrate | | |
|---|---|---|
| 2θ angle | d value | intensity % |
| 4.299 | 20.555 | 21.958 |
| 4.993 | 17.697 | 100.000 |
| 8.181 | 10.807 | 11.750 |
| 8.865 | 9.975 | 14.453 |
| 9.407 | 9.402 | 2.664 |
| 10.142 | 8.721 | 2.181 |
| 10.745 | 8.233 | 4.524 |
| 12.400 | 7.138 | 3.240 |
| 13.309 | 6.652 | 11.178 |
| 14.423 | 6.141 | 33.311 |
| 15.363 | 5.767 | 7.940 |
| 16.537 | 5.360 | 7.382 |
| 17.089 | 5.188 | 12.793 |
| 17.957 | 4.939 | 17.150 |
| 19.408 | 4.573 | 51.933 |
| 20.184 | 4.399 | 47.224 |
| 21.380 | 4.156 | 19.656 |
| 23.055 | 3.858 | 11.874 |
| 24.056 | 3.699 | 7.854 |
| 24.056 | 3.699 | 7.854 |
| 26.896 | 3.315 | 4.200 |
| 28.367 | 3.146 | 6.536 |
| 29.113 | 3.067 | 8.101 |
| 29.777 | 3.000 | 4.704 |
| 30.247 | 2.955 | 5.057 |
| 31.289 | 2.859 | 4.013 |
| 32.413 | 2.762 | 5.311 |
| 33.435 | 2.680 | 3.755 |
| 37.664 | 2.388 | 3.587 |

Preparation of Amorphous Pimavanserin Tartrate

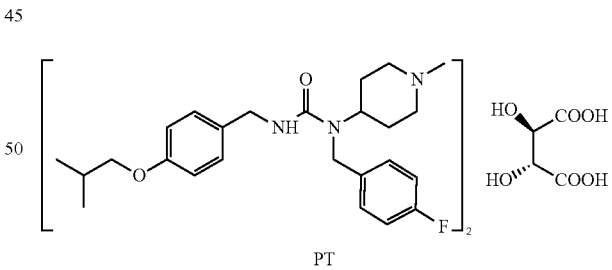

10 g of the sample was added to 40 mL of purified water, and dissolved with stirring at room temperature for 0.5 h. The dissolved solution was filtered through a 0.22 μm filtering membrane, and the filtrate was pre-frozen at −15 to −10° C. for 12 h. A lyophilized dish was transferred to a small lyophilizer for lyophilization. Lyophilization parameters: cold hydrazine temperature −78 to −80° C., vacuum degree<100 Pa, lyophilization time 36-48 h. Finally, 9.8 g of amorphous pimavanserin was obtained (yield 98%). It is determined by differential scanning calorimetry and X-ray powder diffraction that the resulted product is in an amorphous state.

The basic principles, main features and advantages of the present disclosure have been shown and described above. Those skilled in the art should understand that the present disclosure is not limited to the above examples. The above examples and description is only intended to explain the principle of the present disclosure. The present disclosure will also have various modifications and improvements without departing from the spirit and scope of the present disclosure. These modifications and improvements all fall within the protection scope of the present disclosure. The protection scope of the present disclosure is defined by the appended claims and equivalents thereof.

What is claimed is:

1. A method for preparing pimavanserin and a tartrate thereof by using triphosgene, comprising a synthetic route as follows:

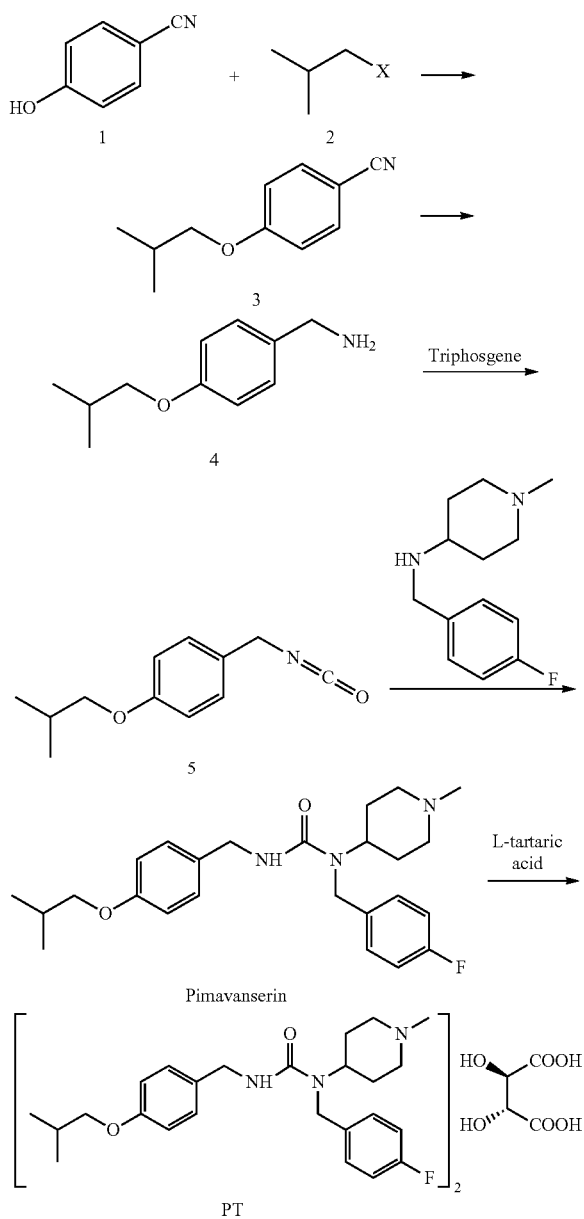

wherein X is halogen; and
wherein the method comprises steps of:
1) taking 4-hydroxybenzonitrile and haloisobutane as raw materials, and performing an etherification reaction to obtain 4-isobutoxybenzonitrile;
2) reducing 4-isobutoxybenzonitrile with $NaBH_4$/nickel chloride hexahydrate to obtain 4-isobutoxybenzylamine;
3) performing an acylation reaction with 4-isobutoxybenzylamine, triethylamine and triphosgene, and concentrating under vacuum to obtain 4-butoxybenzyl isocyanate; and
4) performing a synthetic reaction with 4-butoxylbenzyl isocyanate and N-(4-fluorobenzyl)-1-methyl-piperidin-4-ylamine, to obtain pimavanserin;
optionally, further salinizing with tartaric acid to obtain pimavanserin tartrate.

2. The method according to claim 1, wherein the haloisobutane is at least one of chloroisobutane, bromoisobutane or iodoisobutane.

3. The method according to claim 1, wherein the etherification reaction involves an acid-binding agent which is any one of potassium carbonate, sodium carbonate, sodium hydroxide, potassium hydroxide, potassium bicarbonate, sodium bicarbonate, diisopropyl ethylamine, triethylamine, pyridine, ethylenediamine or triethylenediamine, or a combination thereof.

4. The method according to claim 1, wherein the etherification reaction uses a solvent which is any one of acetone, tetrahydrofuran, acetonitrile, 1,4-dioxane, isopropanol, dimethylformamide or dimethylacetamide, or a combination thereof.

5. The method according to claim 1, wherein the etherification reaction is performed at a temperature of 10 to 110° C.

6. The method according to claim 1, wherein the step of reducing 4-isobutoxybenzonitrile to 4-isobutoxybenzylamine is performed at a temperature of −15 to 70° C.

7. The method according to claim 1, wherein the step of reducing 4-isobutoxybenzonitrile to obtain 4-isobutoxybenzylamine uses a solvent which is tetrahydrofuran, 1,4-dioxane, methylbenzene, methanol, ethanol or isopropanol.

8. The method according to claim 1, wherein the acylation reaction uses an aprotic organic solvent.

9. The method according to claim 1, wherein, in step 4), the synthetic reaction for obtaining pimavanserin uses a solvent which is at least one of dichloromethane, trichloromethane, tetrahydrofuran, 1,4-dioxane, acetonitrile, acetone or methylbenzene.

10. The method according to claim 1, wherein, in step 4), the synthetic reaction for obtaining pimavanserin is performed at a temperature of −15 to 100° C.

11. The method according to claim 1, wherein (4-fluorobenzyl)-N-(1-methylpiperidin-4-yl)-N'-(4-isobutoxybenzyl)urea and tartaric acid are dissolved in a solvent A at a molar ratio of 1:(0.5-0.6) and react at 40 to 80° C., followed by cooling to crystallize and suction filtering to give pimavanserin tartrate;
wherein the solvent A is at least one of anhydrous methanol, anhydrous ethanol, isopropanol, dichloromethane, trichloromethane, methylbenzene, tetrahydrofuran, acetonitrile or ethyl acetate.

* * * * *